United States Patent [19]

New et al.

[11] Patent Number: 6,165,773
[45] Date of Patent: Dec. 26, 2000

[54] METHODS OF PRESERVING VIRUSES

[75] Inventors: Roger Randal Charles New, London; Charles Anthony Hart, Liverpool, both of United Kingdom

[73] Assignee: Provalis UK Limited

[21] Appl. No.: 09/065,734

[22] Filed: Apr. 24, 1998

Related U.S. Application Data

[63] Continuation of application No. PCT/GB96/02615, Oct. 25, 1996.

[30] Foreign Application Priority Data

Oct. 25, 1995 [GB] United Kingdom .................. 9521806

[51] Int. Cl.[7] ...................................................... C12N 7/00
[52] U.S. Cl. ..................... 435/235.1; 435/260; 424/93.6; 424/204.1
[58] Field of Search ................................. 435/260, 235.1; 424/204.1, 93.6

[56] References Cited

FOREIGN PATENT DOCUMENTS

| WO 95/10601 | 4/1995 | WIPO . |
|---|---|---|
| WO 95/13795 | 5/1995 | WIPO . |
| WO 96/14871 | 5/1996 | WIPO . |
| WO 96/17593 | 6/1996 | WIPO . |
| WO 96/17594 | 6/1996 | WIPO . |

*Primary Examiner*—Leon B. Lankford, Jr.
*Attorney, Agent, or Firm*—Pennie & Edmonds LLP

[57] ABSTRACT

Methods for preserving micro-organisms including viruses, such that infectivity is retained, are provided, as well as the use of such methods in preparing e.g. vaccines.

20 Claims, No Drawings

METHODS OF PRESERVING VIRUSES

This application is a continuation of PCT/GB96/02615 filed Oct. 25, 1996.

The present invention relates to methods of preserving micro-organisms such that they retain their infectivity. In particular the invention relates to methods of preserving viral particles.

Storage/viability problems occur in relation to micro-organism storage. In particular problems occur in relation to viral storage where the virus particles are employed for uses such as:

(a) viral vectors for use in, e.g. gene therapy;

(b) storage of viruses for general research progress, e.g. in culture banks;

(c) viruses to be used for release into the environment for control of agricultural pests; and (d) vaccines.

Vaccines comprising viral particles have been in use for a number of years. It is, however, essential that such vaccines can be stored, sometimes for long periods, without the viral component losing its infectivity. Common storage methods include freezing or freeze-drying, the latter usually involving reconstitution using water at a later stage. Unfortunately, certain viruses display reduced viability/infectivity when subjected to these processes.

One virus which is not suitably stored as described above is polio virus. This virus is readily degraded at room temperature in aqueous suspension, is stable for only two weeks at 0° C. and is destroyed by lyophilisation. For this particular virus preferred methods of storage involve freezing at −70° C. or refridgeration at 4° C. However, such storage conditions are not particularly suitable for use in tropical countries or indeed countries where the required facilities and equipment are scarce.

International Application No PCT/GB94/02495 discloses compositions comprising a hydrophilic species solubilised in a hydrophobic phase, as well as methods for their preparation. UK application no. 9424901.8 discloses compositions as described in PCT/GB94/02495 which incorporate additional components which aid retention of the hydrophilic species in the hydrophobic phase. UK application no.9424902.6 discloses compositions as described in PCT/GB94/02495 which incorporate moieties which aid formation of the composition.

In addition, UK patent application no. 9422990.3 discloses immunogenic compositions which comprise an immunogen solubilised, suspended or otherwise dispersed in a hydrophobic phase. The immunogen can be a virus and the compositions are useful as vaccines.

It has now been found that micro-organisms, particularly virus particles, such as polio virus particles, may be converted to a form suitable for long term storage at ambient temperature, with retention of infectivity after reconstitution in aqueous medium. Thus, such compositions have particular advantages for use in countries where the ususal storage methods are less appropriate, and provide an effective means by which such viruses can be transported and stored without the need for extreme freezing or prolonged refridgeration.

Thus, in a first aspect, the present invention provides a method of storing micro-organisms such that they maintain infectivity, which method includes the steps of:

(i) bringing the micro-organisms into association with an amphiphile; and (ii) solubilising, suspending or otherwise dispersing the micro-organisms in a hydrophobic phase.

In one preferred embodiment the micro-organisms are virus particles particularly polio virus particles.

Suitable methods for carrying out the above method are those described in PCT/GB94/02495, UK 9424901.8, UK 9424902.6 and UK 9422990.3.

The hydrophobic solvent could for example be a long chain fatty acid, a medium chain alcohol, a branched long chain alcohol, a monoglyceride, a diglyceride, a medium chain triglyceride, a long chain triglyceride, a halogenated (e.g. fluorinated) analogue thereof, or a polyoxyethylene-containing lipid.

In particular embodiments the hydrophobic solvent is a mono-, di- or tri-glyceride, or oleic acid.

In one preferred embodiment the method comprises:

(i) co-dispersing the micro-organisms with an amphiphile in a liquid medium;

(ii) removing the liquid medium to leave an array of amphiphile molecules with their hydrophilic head groups orientated towards the micro-organism; and (iii) providing a non-aqueous solvent around the micro-organisms/amphiphile array.

The liquid medium can be water, and it can be removed by, e.g. freeze drying, centrifugal vacuum drying or any other suitable method.

Suitably, in the above methods the amphiphile will be a phospholipid, for instance one with a phosphatidyl choline head group, eg phosphatidyl choline (PC), lysophosphatidyl choline(lyso-PC), sphingomyelin or a derivative of one of these such as hexadecyl phosphocholine or an amphiphile polymer containing phosphoryl choline. A bile salt, a glycolipid, a polyoxyethylene containing surfactant, a lipophilic sulphate, betaine, a sarcosine containing surfactant, Solulan C24 (polyoxyethylene-24-cholesteryl ether), polyoxyethylene 40 stearate, one of the Tween series of surfactants (polyoxyethylenesorbitan surfactants), one of the Span series of surfactants (sorbitan monolaurate, sorbitan monooleate, sorbitan monopalmitate, sorbitan monostearate, sorbitan trioleate and sorbitan tristearate) or a pegolated castor oil derivative, e.g. Cremaphor EL35.

Without wishing to be bound by the following, it is believed that in the methods described above the micro-organisms, eg virus particles, first form an array with the amphiphile molecules. This array is then in turn coated with the hydrophobic solvent. In this way access to the micro-organisms by water is restricted, which in turn accounts for the improved storage properties when the micro-organism preparation is reconstituted from a freeze-dried state.

In a second aspect, the present invention provides a method of storing micro-organisms such that they retain infectivity, which method includes the following steps:

(i) bringing the micro-organisms into association with an amphiphile in an aqueous phase; and (ii) removing the water.

Preferably, the water is removed by freeze-drying.

The amphiphile can be a phospholipid, for instance one with a phosphatidyl choline head group, eg phosphatidyl choline (PC), lysophosphatidyl choline(lyso-PC), sphingomyelin or a derivative of one of these such as hexadecyl phosphocholine or an amphiphile polymer containing phosphoryl choline. A bile salt, a glycolipid, a polyoxyethylene containing surfactant, a lipophilic sulphate, betaine, a sarcosine containing surfactant, Solulan C24 (polyoxyethylene-24-cholesteryl ether), polyoxyethylene 40 stearate, one of the Tween series of surfactants (polyoxyethylene sorbitan surfactants), one of the Span series of surfactants (sorbitan monolaurate, sorbitan monooleate, sorbitan monopalmitate, sorbitan monostearate, sorbitan trioleate and sorbitan tristearate) or a pegolated castor oil derivative, e.g. Cremaphor EL35.

In a particularly preferred embodiment of this aspect the amphiphile is Solulan C24, polyoxyethylene 40 stearate, one of the Tween series of surfactants, one of the Span series of surfactants or a pegolated castor oil derivative, e.g Cremaphor EL35. In particularly preferred embodiments the amphiphile is Solulan C24 or polyoxyethylene 40 stearate.

It is possible that upon removal of the water the amphile/micro-organism array will be in an "open" form. Thus, upon reconstitution water may still have access to the micro-organisms and this will lead to loss of infectivity. Therefore, in another preferred embodiment of this aspect of the invention the method also includes the step of elevating the temperature of the mixture after removal of the water. This ensures that the structure adopted by the amphiphile/micro-organism array is more condensed, which in turn results in more restricted access for water upon reconstitution.

When the heating step is employed, the amphiphile will be one which remains solid after the water removal step, eg it can be chosen from a phospholipid, for instance lecithin, a glycolipid, a polyoxyethylene containing surfactant, a lipophilic sulphate, betaine, a sarcosine containing surfactant, Solulan C24, polyoxyethylene 40 stearate, one of the Tween series of surfactants, one of the Span series of surfactants or a pegolated castor oil derivative, e.g. Cremaphor EL35.

In other aspects the invention provides:

i) a micro-organism composition obtainable by any of the methods described herein, particularly a micro-organism composition comprising virus particles, eg polio virus particles; and ii) the use of a composition of the invention for the storage of virus particles.

Preferred features of each aspect of the invention are as for each other aspect mutatis mutandis.

The invention will now be described with reference to the following example, which should not be construed as in any way limiting the invention.

EXAMPLE 1

A suspension of $10^9$ polio virus particles (Sabin strains, Types 1, 2, 3) per ml of culture was diluted 1000-fold in distilled water. 1 ml of the diluted suspension was mixed with 1 ml of adispersion of sonicated soya phospholipid (at a concentration of 100 mg/ml) in distilled water. A control vial was prepared which contained virus only, without the addition of phospholipid.

The contents of both vials were shell-frozen in liquid nitrogen and lyophilised overnight. The following day, 1 ml of oleic acid was added to the vial containing virus and phospholipid, and the contents of the vial wre then mixed on a roller mixer for several hours. A clear solution was obtained.

A control vial of polio virus was prepared as above. To this control vial, containing virus alone, was added 1 ml of culture medium.

10 µl of oil/virus preparation was transferred to a fresh vial, and 1 ml of a 2% solution of ox bile extract (containing predominantly sodium taurocholate) was added. The mixture was shaken well to disperse the oil in water, with the intention of releasing particles into the aqueous phase. Ten-fold serial dilutions were made in culture medium, and 0.5 ml of each dilution was added to confluent monolayers of Viro cells, and incubated for four days, to test for the presence of intact virus. An identical procedure was followed for the contents of the control vial. Growth was assessed by visual observation of virus-induced cell lysis in each monolayer. Growth was recorded in the two series of dilutions as follows:

| Dilution of lyophilisate | $10^2$ | $10^3$ | $10^4$ | $10^5$ | $10^6$ |
|---|---|---|---|---|---|
| Virus particles present (per ml) | $10^4$ | $10^3$ | $10^2$ | 10 | 1 |
| Oil-based lyophilisate | + | + | + | + | − |
| Oil-free lyophilisate | + | + | − | − | − |

These results indicate that the method of the present invention clearly improves the viability of stored viral preparations, when compared to lyophilisation alone.

EXAMPLE 2

A virus suspension (Sabin strains, Types 1, 2, 3) containing $5 \times 10^8$ particles/ml (spun to remove contaminating protein) was diluted 50-fold by addition of 200 µl of the suspension to 9.9 ml of distilled water, yielding a concentration of $10^7$ particles/ml. The suspension was divided into four equal aliquots of 2.5 ml, and dispensed into 7 ml screw-capped glass vials. One aliquot was employed in the experiment described herein, while two were used in the experiment described in example 3.

2.5 ml of sonicated phospholipid dispersion (100 mg/ml) was added to the aliquot of diluted virus particles with gentle mixing. 200 µl of this mixture was dispensed into 20 freeze-drying vials, and the remainder was transferred, In 100 µl aliquots, into other tubes as "pre-drying" controls. The controls were stored overnight at +4° C. The freeze-drying vials were placed in the centrifugal rotor of the freeze-dryer and lyophilised overnight.

On the following day 100 µl of culture medium was added to the contents of ten of the vials freeze-dried overnight, while 100 µl of oleic acid (B.P.) was added to the other ten. The groups were labelled "M" and "O" respectively. 10 µl of samples from two "M" labelled tubes were transferred to fresh 1 ml vials, and 1 ml of 0.1 M bicarbonate solution containing 25 mg/ml sodium taurocholate was added and mixed well. Under these conditions the oil was dispersed well to give a clear solution.

4×20 µl aliquots of sample were transferred from the pre-drying control group stored overnight at +4° C. to fresh 1 ml vials. To two of these vials was added 1 ml of medium, while to the other two was added 1 ml of 0.1M bicarbonate solution containing 25 mg/ml sodium taurocholate. The contents of each of the vials was mixed well.

The suspensions prepared above were used to perform 10-fold dilutions in Vero cell monolayer cultures, in order to measure the viability of the polio virus present. the results were expressed as the highest dilution at which 50% cytopathic effects were observed.

| Nature of sample | Highest dilution at which 50% CPE observed |
|---|---|
| Non-dried control in medium | $10^{-4}/10^{-5}$ |
| Non-dried control in taurocholate | $10^{-3}/10^{-3}$ |
| Oil-free lyophilate in medium | $10^{-1}/10^{0}$ |

-continued

| Nature of sample | Highest dilution at which 50% CPE observed |
| --- | --- |
| Oil-free lyophilate in taurocholate | $10^{-1}/10^{-1}$ |
| Oil-based lyophilate in taurocholate | $10^{-6}/10^{-6}$ |

EXAMPLE 3

2.5 ml of distilled water was added to one aliquot of virus particles prepared as described in example 2, and this group was labelled "W". 2.5 ml of Solulan C24 (100 mg/ml) was added to another aliquot and mixed gently. This group was labelled "S".

200 μl of each preparation was dispensed into 10 freeze-drying vials, and the remainder in 100 μl aliquots into other tubes as "pre-drying" controls. The controls were stored overnight at +4° C. The freeze-drying vials were placed in the centrifugal rotor of the freeze-dryer and lyophilised overnight.

On the following day 100 μl of culture medium was added to each vial in group "W" and mixed gently. The vials in group "S" were sealed and heated to 60° C. in a hot water bath for 5 seconds to melt the Solulan C24, which resulted in a claer solution. Upon cooling to room temperature this material solidified. 90 μl of medium was added to the vials of the "S" group to make the total volume up to 100 μl. 10 μl of sample was then transferred from each of groups "S" and "W" to fresh 1 ml vials and 1 ml of medium was added to each and mixed well.

To fresh 1 ml vials was added 4×20 μl of samples from each of the pre-drying groups and 1 ml of medium was added to each. The contents of each vial were mixed well.

The suspensions prepared as described herein were used to perform 10-fold dilutions in Vero cell cultures, to measure the viability of the polio virus present. The results were expressed as the highest dilution at which 50% cytopathic effects were observed.

| Nature of Sample | Highest Dilution at which 50% CPE observed |
|---|---|
| Non-dried control + water | $10^{-4}/10^{-6}$ |
| Non-dried control + Solulan C24 | $10^{-5}/10^{-5}$ |
| Freeze-dried control + water | $10^{-2}/10^{-2}$ |
| Freeze-dried control + Solulan C24 | $10^{-6}/10^{-8}$ |

What is claimed is:

1. A method for preparing virus particles for storage such that they retain infectivity, which method includes the steps of:

(i) mixing virus particles with an amphiphile in a liquid medium;

(ii) removing the liquid medium to leave an array of amphiphile molecules with their hydrophilic head groups orientated towards the virus particles; and (iii) mixing the virus particles/amphiphile array with a hydrophobic solvent.

2. A method as claimed in claim 1 wherein the virus particles are polio virus.

3. A method as claimed in claim 1 wherein the hydrophobic solvent is a long chain fatty acid, a medium chain alcohol, a branched long chain alcohol, a monoglyceride, a diglyceride, a medium chain triglyceride, a long chain triglyceride, a halogenated analogue thereof or a polyoxythylene-containing liquid.

4. A method as claimed in claim 3 wherein the hydrophobic solvent is mono-, di- or tri-glyceride.

5. A method as claimed in claim 3 wherein the hydrophobic solvent is oleic acid.

6. A method as claimed in claim 1 wherein the amphiphile is a phospholipid, a bile salt, a glycolipid, a polyoxyethylene-containing surfactant, a lipophilic sulphate, betaine, a sarcosine containing surfactant, polyoxyethylene-24-cholesteryl ether, polyoxyethylene 40 stearate, one of the polyoxyethylenesorbitan surfactants, sorbitan monolaurate, sorbitan monooleate, sorbitan monopalmitate, sorbitan monostearate, sorbitan trioleate, sorbitan tristearate or a pegolated castor oil derivative.

7. A method as claimed in claim 6 wherein the amphiphile is a phospholipid which is phosphatidyl choline (PC), lyso-phosphatidyl choline (lyso-PC), sphingomyelin, hexadecyl phosphocholine or an amphiphile polymer containing phosphoryl choline.

8. A method for preparing virus particles for storage such that they retain infectivity, which method includes the following steps:

(i) mixing virus particles with an amphiphile in an aqueous solvent;

(ii) removing the water; and (iii) mixing the product from step (ii) with a hydrophobic solvent.

9. A method as claimed in claim 8 wherein the water is removed by freeze drying.

10. A method as claimed in any one of claims 8 or 9 wherein the amphiphile is a phospholipid, a bile salt, a glycolipid, a polyoxyethylene-containing surfactant, a lipophilic sulphate, betaine, a sarcosine containing surfactant, polyoxyethylene-24-cholesteryl ether, polyoxyethylene 40 stearate, one of the polyoxyethylenesorbitan surfactants, sorbitan monolaurate, sorbitan monooleate, sorbitan monopalmitate, sorbitan monostearate, sorbitan trioleate, sorbitan tristearate or a pegolated castor oil derivative.

11. A method as claimed in claim 10 wherein the amphiphile is polyoxyethylene-24-cholesteryl ether, polyoxyethylene 40 stearate, one of the polyoxyethylenesorbitan surfactants, sorbitan monolaurate, sorbitan monooleate, sorbitan monopalmitate, sorbitan monostearate, sorbitan trioleate, sorbitan tristearate or a pegolated castor oil derivative.

12. A method as claimed in claim 11 wherein the amphiphile is polyoxyethylene 40 stearate.

13. A method as claimed in claim 11 wherein the amphiphile is Solulan C24.

14. A method as claimed in claim 8 wherein the mixture of amphiphile and virus particles is converted to a condensed form by elevating the temperature of the mixture after removal of the water.

15. A method as claimed in claim 8 wherein the virus particles are polio virus particles.

16. A method as claimed in claim 8 wherein the hydrophobic solvent is a long chain fatty acid, a medium chain alcohol, a branched long chain alcohol, a monoglyceride, a diglyceride, a medium chain triglyceride, a long chain triglyceride, a halogenated (e.g., fluorinated) analogue thereof or a polyoxythylene-containing lipid.

17. A virus composition obtainable by a method as defined in any one of claims 1 or 8.

18. A virus composition as claimed in claim 17 comprising polio virus particles.

19. A method for preparing a vaccine composition, comprising providing a virus composition obtainable by the method of claim 1 or 8 to form a vaccine composition useful to induce an immune response in a subject.

20. A method to prepare an agent capable of inducing an immune response in a subject, providing a virus obtainable by the method of claim 1 or 8.

* * * * *